United States Patent
Priewe et al.

(10) Patent No.: US 9,205,179 B2
(45) Date of Patent: *Dec. 8, 2015

(54) BROAD-SPECTRUM ANTIMICROBIAL COMPOSITIONS BASED ON COMBINATIONS OF TAUROLIDINE AND PROTAMINE AND MEDICAL DEVICES CONTAINING SUCH COMPOSITIONS

(71) Applicant: Ethicon, Inc., Somerville, NJ (US)

(72) Inventors: Joerg Priewe, Kiel (DE); Xintian Ming, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/900,519

(22) Filed: May 22, 2013

(65) Prior Publication Data

US 2013/0251774 A1 Sep. 26, 2013

Related U.S. Application Data

(63) Continuation of application No. 13/248,290, filed on Sep. 29, 2011.

(51) Int. Cl.

| | | |
|---|---|---|
| A01N 37/18 | (2006.01) | |
| A01N 59/16 | (2006.01) | |
| A01N 59/04 | (2006.01) | |
| A01N 25/34 | (2006.01) | |
| B05D 7/00 | (2006.01) | |
| A01N 25/08 | (2006.01) | |
| A01P 1/00 | (2006.01) | |
| A61P 31/00 | (2006.01) | |
| A61K 38/17 | (2006.01) | |
| B05D 5/00 | (2006.01) | |
| A01N 59/20 | (2006.01) | |
| A01N 25/10 | (2006.01) | |

(Continued)

(52) U.S. Cl.
CPC ............ *A61L 31/047* (2013.01); *A61F 2/12* (2013.01); *A61K 31/549* (2013.01); *A61K 38/16* (2013.01); *A61K 45/06* (2013.01)

(58) Field of Classification Search
CPC ................................. A61K 2300/00
See application file for complete search history.

(56) References Cited

U.S. PATENT DOCUMENTS

2005/0233950 A1 10/2005 Madhyastha
2007/0048433 A1* 3/2007 Hallett et al. .............. 427/2.1

(Continued)

FOREIGN PATENT DOCUMENTS

| JP | 4258276 A | 9/1992 |
|---|---|---|
| JP | 2009091322 A | 4/2009 |
| WO | WO 2005/018701 A1 | 3/2005 |

OTHER PUBLICATIONS

Miller, B F; Abrams, R; Dorfman, A; Klein, M ,"Antibacterial Properties of Protamine and Histone" Science 96(2497):428-30, Nov. 6, 1942.

(Continued)

*Primary Examiner* — Scott Long
*Assistant Examiner* — Sarah Alawadi
(74) *Attorney, Agent, or Firm* — E. Richard Skula (57) ABSTRACT

Novel antimicrobial compositions and coatings are disclosed. The antimicrobial compositions consist of mixtures of taurolidine and protamine, including protamine salts. The antimicrobial compositions are particularly useful in coatings for implantable medical devices. The antimicrobial compositions are effective against a broad spectrum of microbes.

13 Claims, 2 Drawing Sheets

*In-vitro* Efficacy of Taurolidine (TAU), Protamine Sulfate (PS) and Synergistic Mixtures Thereof against S. aureus (in SST, 37°C, 24h)

(51) Int. Cl.
  *A61L 31/04* (2006.01)
  *A61K 38/16* (2006.01)
  *A61K 31/549* (2006.01)
  *A61F 2/12* (2006.01)
  *A61K 45/06* (2006.01)

(56) References Cited

U.S. PATENT DOCUMENTS

2007/0093894 A1* 4/2007 Darouiche ............... 623/11.11
2007/0202177 A1* 8/2007 Hoang ..................... 424/486
2011/0290799 A1* 12/2011 Anderson et al. ......... 220/200

OTHER PUBLICATIONS

Lee, C.K.; Rubin, L.G.; Moldwin, R.M.,"Synergy Between Protamine and Vancomycin in the Treatment of *Staphylococcus epidermidis* Biofilms", Urology 45(4):720-724, Apr. 1995.
Johansen, C; Verheul, A; Gram, L; Gill, T; Abee, T , "Protamine-Induced Permeabilization of Cell Envelopes of Gram-Positive and Gram-Negative Bacteria", Applied and environmental microbiology 63(3):1155-9,Mar. 1997.
Boussard, P; Devleeschouwer, M; Dony, J ., "Influence of Protamine on the In Vitro Sensitivity of *Pseudomonas aeruginosa* to Antibiotics", Pharmaceutica Acta Helvetiae,68(3):161-7, Jan. 1994.

* cited by examiner

FIG.1: *In-vitro* Efficacy of Taurolidine (TAU), Protamine Sulfate (PS) and Synergistic Mixtures Thereof against S. aureus (in SST, 37°C, 24h)

FIG.2 : *In-vitro* Efficacy of Low Dose Taurolidine (TU), Protamine Sulfate (PS) and Synergistic Mixtures Thereof against E. coli (in serum, 37°C, 24h)

BROAD-SPECTRUM ANTIMICROBIAL COMPOSITIONS BASED ON COMBINATIONS OF TAUROLIDINE AND PROTAMINE AND MEDICAL DEVICES CONTAINING SUCH COMPOSITIONS

CROSS REFERENCE TO RELATED APPLICATION

This application is a continuation of application Ser. No. 13/248,290 filed on Sep. 29, 2011, now U.S. Publication No. US2013/0084319A1, published on Apr. 4, 2013.

FIELD OF THE INVENTION

The field of art to which this invention relates is antimicrobial compositions, more specifically combinations of taurolidine and protamine for use with medical devices.

BACKGROUND OF THE INVENTION

Hospital acquired infections are of great concern to health care providers and patients. Relatively routine surgical procedures can have disastrous health consequences when a patient acquires an infection at the surgical site, even though the underlying surgical procedure was successful. Hospitals and health care providers have instituted infection control and prevention protocols and precautions to reduce the incidence of hospital acquired infections. These include sterile fields in the operating room, instrument sterilization procedures, gowning and gloves, HEPA filtered air streams, antimicrobial wipedowns of the patient's skin surrounding the surgical site prior to initiating the procedure, cleaning protocols, etc. However, notwithstanding such procedures and protocols, whenever a medical device is used in a surgical setting, a risk of infection is created, even though the medical device itself is sterile as provided in its packaging. The risk of infection dramatically increases for invasive or implantable medical devices, such as intravenous catheters, arterial grafts, intrathecal or intracerebral shunts, meshes, sutures, sealants and prosthetic devices, which create a portal of entry for pathogens while in intimate contact with body tissues and fluids. The occurrence of surgical site infections is often associated with bacteria that colonize on a medical device and form biofilms. For example, during a surgical procedure, bacteria from the surrounding environment may enter the otherwise sterile field surrounding a surgical site and attach to a medical device that is either in contact with the patient or implanted into the patient. Bacteria can then use the implanted medical device as a pathway to surrounding tissue. Such bacterial colonization on the medical device may lead to an infection resulting in morbidity and mortality.

A number of methods for reducing the risk of infection associated with invasive or implantable medical devices have been developed that incorporate antimicrobial agents into or onto the medical devices, for example, antimicrobial coatings or compounding polymeric materials with such agents. Such devices desirably provide sufficiently effective levels of antimicrobial agent to counteract any bacterial contamination that might have entered the patient for a period of time after the device is in place, including inhibiting the formation of difficult to treat biofilms. Conventional antimicrobial compositions that have been used with implantable medical devices include triclosan, silver, and chlorhexidine gluconate, and may also include antibiotics such as rifampin, minocycline, clindamycin and gentamicin. However, it can be appreciated that the use of antibiotics for this purpose raises concerns with respect to antibiotic resistance. Such resistance is typically not present with antimicrobials that are not antibiotics.

Antimicrobial compositions for use in treating medical devices are known in the art. The compositions may be applied to the devices via conventional coating processes, or may be compounded into polymer compositions used to manufacture the devices. However, a distinction is drawn between devices that are implanted into the body versus devices that may have limited contact with body tissue and bodily fluids. The toxicity of an efficacious antimicrobial composition which is useful with a device that is not designed for implantation may preclude the use of that antimicrobial in or on an implantable device. This is especially true with large implants having correspondingly large surface areas.

One particular challenge with regard to making large-sized antimicrobial implant devices, such as surgical meshes, relates to applying safe and effective amounts of antimicrobial compositions sufficient to protect the implant from bacterial colonization after implantation, while producing no harmful side effects to patients and retaining the functionality of the devices. Taurolidine is known to be a mild antibacterial agent with a history of safe internal (in vivo) use, and thus has the potential to be used safely with implantable medical devices. One challenge associated with using Taurolidine on, or in, an implantable medical device is the large quantity of the antimicrobial composition typically required in order to be efficacious. This may affect several functional aspects of the device, including the appearance (e.g., flecking) and handling (e.g., flexibility) of the device. In addition, large quantities of any antimicrobial may have some toxic effects after implantation. The degree of toxicity is often correlated with the quantity or amount of the antimicrobial present on or in the device.

The use of taurolidine is often associated with catheter or fluid locks. Protamine sulfate is also known to be used with such locks as an anticoagulant. Such uses do not contemplate long term implanted medical devices, since anticoagulants are often contraindicated for obvious reasons.

Therefore, there is a need for new and improved, safe and efficacious, antimicrobial compositions for use with implantable medical devices that have improved antimicrobial performance while utilizing decreased amounts of the compositions.

SUMMARY OF THE INVENTION

Accordingly, novel antimicrobial compositions are disclosed. The antimicrobial compositions are useful with implantable medical devices. The compositions consist of about 50 wt. % to about 99 wt. % of taurolidine and about 1 wt. % to about 50 wt. % of protamine or a protamine salt.

Another aspect of the present invention is a medical device having at least a section or portion of a surface coated with the above-described antimicrobial composition. In a preferred embodiment, the medical device is implantable.

Yet another aspect of the present invention is an antimicrobial coating composition containing the above-described antimicrobial composition. The coating composition is especially useful with implantable medical devices.

Still yet another aspect of the present invention is a method of coating at least a section or portion of a surface of a medical device with the above-described antimicrobial composition or antimicrobial coating composition. The method is especially useful for implantable medical devices.

A further aspect of the present invention is a medical device made from a combination of a polymer resin and the above-described anti-microbial composition. In a preferred embodiment the devices are implantable.

These and other features and advantages of the present invention will become more apparent from the following description and accompanying drawings.

DETAILED DESCRIPTION OF THE INVENTION

The term implantable medical devices as used herein is defined to have its conventional meaning and refers to any device or implant made from a biocompatible material for insertion or implantation into the body of a human or animal subject, including but not limited to stents (e.g., coronary stents, vascular stents including peripheral stents and graft stents, urinary tract stents, urethral/prostatic stents, rectal stents, esophageal stents, biliary stents, and pancreatic stents), surgical sutures, surgical needles, meshes, electrodes, catheters, leads, implantable pacemakers, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc., and equivalents thereof.

The implantable medical devices may be formed from any suitable conventional biocompatible material, including but not limited to polymers (including stable or inert polymers, organic polymers, organic-inorganic copolymers, inorganic polymers, and biodegradable polymers), metals, metal alloys, inorganic materials such as silicon, glasses, and composites thereof, including layered structures with a core of one material and one or more coatings of a different material. The materials may be bioabsorbable, partially bioabsorbable, or nonabsorbable. The term bioabsorbable as used herein is defined to have its conventional meaning as being essentially a polymeric material that is absorbed from the locus of implantation in less than three years. Wherein the bioabsorbable polymer may be biodegradable whereby the backbone or sidechains degrade or dissolve into lower molecular weight polymers that are metabolized and/or excreted from the body.

The bioabsorbable polymers may include conventional biocompatible bioabsorbable polymers including, but not limited to, polyethers such as polyethylene glycol or polyethyleneoxide, polyvinylpyrroldine, polyvinylalcohol, polyhydroxy acids, polylactides, polyglycolides, polyhydroxy butyrates, polyhydroxy valeriates, polycaprolactones, polydioxanones, synthetic and natural oligo- and polyamino acids, polyphosphazenes, polyanhydrides, polyorthoesters, polyoxaesters, polyphosphates, polyphosphonates, polyalcohols, polysaccharides, polyethers, polyamides, aliphatic polyesters, aromatic polyesters, copolymers of polymerizable substances thereof, and resorbable bioglasses. The nonabsorbable polymers may include conventional biocompatible polymers including, but not limited to, polyalkenes, polypropylene, polyethylene, partially halogenated polyolefins, wholly halogenated polyolefins, fluorinated polyolefins, polytetrafluorethylene, polyvinylidene fluoride, polyisoprenes, polystyrenes, polysilicones, polycarbonates, polyarylether ketones, polymethacrylic acid esters, polyacrylic acid esters, polyimides, non degradable polysaccharides such as cellulose, bacterial cellulose, and copolymers of polymerizable substances thereof.

The components of the antimicrobial compositions of the present invention include a methylol-containing compound such as taurolidine and protamine, or preferably a particular a protamine salt such as protamine sulfate or protamine hydrochoride, optionally in a solvent or coating solution.

By "methylol-containing compound," or "methylol transfer agent," is meant a compound which contains or is capable of producing a methylol molecule under physiological conditions. A methylol-containing compound is characterized as having a R—CH2-OH group in which R is an alkyl, aryl or hetero group. The invention also includes the use of compounds capable of producing or being converted into a compound containing an R—CH2-OH structure.

Taurolidine (bis(1,1-dioxoperhydro-1,2,4-thiadiazinyl-4)-methane) is a derivative of the amino acid taurine and has antimicrobial properties. Taurolidine is believed to act via a chemical reaction with bacterial cell wall structures. Bacteria exposed to the compound are killed and released toxins are inactivated. Taurolidine has been shown to be safe and well tolerated at systemic doses exceeding 40 g/day and cumulative doses up to and exceeding 300 g. Taurolidine has been used to treat patients with peritonitis and used as a catheter lock solution for the prevention of central venous catheter-related infections. Compared to other known antimicrobial compositions used on medical devices, the antimicrobial properties of taurolidine are relatively weaker, therefore more dosing is needed for efficacy. Even though the quantities of taurolidine required to achieve efficacy on a particular medical device may be safe and biocompatible, the physical properties of a coating on the medical device containing such a relatively high dose might be adversely impacted and affected. Therefore, a highly effective composition having reduced amounts of the antimicrobial agent is needed for taurolidine use on medical devices. Taurolidine-like compounds like Taurultame (38668-01-8), Cyclotaurolidine (220928-22-3) or similar acting molecules like Cilag 61 (531-18-0) or Noxiflex S (15599-39-0) may be used alternatively or in combination with taurolidine in the practice of the present invention.

Protamine is a small arginine-rich, highly cationic peptide. Protamine was discovered combined with nucleic acids in the sperm of certain fish, and has the property of neutralizing heparin. Protamine sulfate is usually administered to reverse a large dose of heparin administered during certain surgeries. Protamine may also be used in its free form and in the form of a salt. A suitable protamine useful in the practice of the present invention is, for example, protamine sulfate or protamine hydrochloride. In the practice of the present invention it is preferred that pharmagrade-approved protamine (USP grade) sources are used.

Protamine is also used as a mixture of peptides. According to Hvass (2005), Hvass A and Skelbaek-Pedersen B, *J. Pharm Biomed Anal* 37(3):551-7 (2005), commercially available protamines are usually obtained as the sulphate salt, and for insulin formulations, salmine protamine from fish of the family Salmonidae is normally used. Salmine protamine may be classified as a mono-protamine as only one basic amino acid, Arginine, is present. The four major peptides, which constitute almost the entire nitrogen containing material in salmine protamine, have been fully characterized.

According to Block (1937), *Yale J Biol Med.* 1937 May; 9(5): 445-503, the protamines have been divided into four groups depending on their content of the major or basic amino acids; those containing
(1) arginine only (monoprotamines)
(2) arginine and lysine (diprotamines)
(3) arginine and histidine (diprotamines)
(4) arginine, histidine, and lysine (triprotamines)
Examples of protamines and hydrolizates or fragments thereof that are useful are described below.

```
Hydrolized protamine
(1030905-03-3, Sequence: 1 RRRRGGRRRR)

Low Molecular Weight Protamine
(121052-30-0, Sequence Length: 14,
Sequence: 1 VSRRRRRRGG RRRR)

Low Molecular Weight Protamine
(756860-86-3, Sequence Length: 6,
Sequence: 1 PRRRRR)

Low Molecular Weight Protamine
(756860-88-5, Sequence Length: 13,
Sequence: 1 ASRRRRRGGR RRR)

Low Molecular Weight Protamine
(1115247-45-4, Sequence Length: 10,
Sequence: 1 PRRRRSSPPR)

Stelline C
(142847-28-7, Sequence Length: 26,
Sequence: 1 RRRRRHASTK LKRRRRRRRH GKKSHK)

Protamine 1a
(Oncorhynchus mykiss testis) (78473-81-1,
Sequence Length: 30, Sequence: 1 PRRRRASRRV
RRRRRPRVSR RRRRGGRRRR)

Protamine
(rat sperm reduced) (119370-87-5,
Sequence Length: 50 Sequence:
1 ARYRCCRSKS RSRCRRRRRR CRRRRRRCCR
RRRRRCCRRR RSYTFRCKRY)

1 Protamine St 1 (horse sperm reduced)
(110616-21-2, Sequence Length: 49,
Sequence: ARYRCCRSQS QSRCRRRRRR RCRRRRRRSV
RQRRVCCRRY TVLRCRRRR)

Protamine (Dicentrarchus labrax)
(147414-03-7Sequence Length: 34
Sequence: 1 PRRRRQASRP VRRRRRTRRS
TAERRRRRVV RRRR)

Ecmolin (8001-16-9) a Triprotamin
```

Additional Protamine-like molecules which are acting as anti-heparin agents such as Polybrene, Terlipressin, Romiplostim, Eltrombopag, or condensed DNA like Polyarginine, Polylysin and finally protamine-like proteins or protamine-like peptides which are a group of sperm nuclear basic proteins (SNBPs) together with protamine type and histone type. Protamine-like SNBPs represent the most structurally heterogeneous group, consisting of basic proteins which are rich in both lysine and arginine amino acids. Additional protamine-like peptides are described sometimes according to U.S. Pat. No. 5,614,494 as are synthetic protamine-like polycationic peptides having a total cationic charge which is less than that of n-protamine.

Additional Protamine like molecules can have the same mode of action in the case of sustained insulin formulations like Surfen (dihrochloride 5424-37-3 or base 3811-56-1), globin optional with a trace of zink.

The amount of taurolidine and protamine in the antimicrobial compositions of the present invention will be sufficient to provide effective antimicrobial activity without exhibiting any significant levels of toxicity. Typically the amount of taurolidine present in the antimicrobial compositions will be about 50 wt. % to about 99 wt. %, more typically about 60 wt. % to about 90 wt. %, and preferably about 70 wt. % to about 90 wt. %. The amount of protamine or protomine salt present in the antimicrobial compositions will typically be about 1 wt. % to about 50 wt. %, more typically about 5 wt. % to about 50 wt. %, and preferably about 10 wt. % to about 50 wt. %.

The antimicrobial compositions of the present invention may be utilized with medical devices to provide an antimicrobial effect in a variety of ways. The compositions may be included in coating compositions and coated onto surfaces of medical devices using conventional coating processes including dipping, brushing, and spraying. The antimicrobial compositions may also be incorporated into medical devices in other conventional manners, including compounding into a resin, and then extruding or molding a medical device from the resulting compounded resin.

Conventional techniques and processes may be used to apply the compositions and coatings of the present invention onto the surfaces of medical devices and implants. The techniques include, but are not limited to, dip coating, spraying, inkjet (solvent jet) application, swelling, powder coating with sintering, injection molding, and plasma or laser deposition coating, etc. As mentioned previously above, if desired, the antimicrobial compositions of the present invention may be compounded or blended with polymeric materials, which are then used as mixtures or blends in solid or semi-solid form as granules or powders. Such polymeric mixtures or blends may then be processed in conventional manners including, but not limited to, compressed into tablets, extruded, injection molded, etc.

In one preferred embodiment, the antimicrobial coatings of the present invention are applied as liquid coating compositions. The liquid coating compositions will typically utilize one or more liquid solvents or carriers, and depending upon the indication, different solvent systems may be used.

The conventional solvents that are optionally included in the antimicrobial coating compositions of the present invention include, but are not limited to, water for injection, ethanol/water mixtures, isopropanol water mixtures, glycerol/water mixtures, protein solutions, and blood and serum. If desired, additional conventional biocompatible components may be included in the antimicrobial compositions of the present invention when used as a coating composition including surfactants, thickeners, polyvinylpyrrolidones, polyethyleneglycols, carboxymethylcellulose, hydroxyethylstarch, hydroxypropyl starch, dextrane, polyoxypropylene-polyoxyethylene copolymers, polyethoxylated castor oils, etc., and combinations thereof. The antimicrobial coatings of the present invention will contain a sufficient amount of the antimicrobial compositions of the present invention to provide an effective antimicrobial effect without exhibiting significant levels of toxicity. For example, the amount of the antimicrobial compositions of the present invention contained in the coating compositions will typically be about 0.1 wt. % to about 10 wt. %, more typically about 2 wt. % to about 4.5 wt. %, and preferably about 2 wt. %, with the remainder being solvent or solvents and other optional additives. Those skilled in the art will appreciate that these amounts may vary depending upon several factors including the size and shape of the medical device, the location of the implanted device in the body, the composition of the implanted device, the age and weight of the patient, the duration of the length of time that the implant will remain in the patient's body, the surface area of the implant, etc.

When using the antimicrobial compositions of the present invention in an antimicrobial coating composition, the coating compositions can be prepared in a conventional manner. For example, a required amount of the antimicrobial composition is admixed with solvent in a conventional mixing vessel in the following manner. A suitable, conventional vessel is provided with a stirring device such as a magnet stirring bar or a paddle stirrer. A solvent or solvent mixture is added to the vessel and a defined amount of protamine or protamine salt such as protamine sulfate is added to the vessel under stirring. The mixture is warmed if or as needed, and a defined amount of taurolidine is added. Any additional solvent/solvent mixture as needed is added to adjust the final concentration of said mixture. Those skilled in the art will appreciate that additional conventional biocompatible components may be added to the coating compositions including resins, surfactants, pigments, etc.

For injection or internal use such as intraperitoneal lavage basically water-based systems are preferred, e.g., Ringer, isotonic NaCl or Glucose. The pH can be adjusted with HCl, H2SO4 or Phosphoric acid for a pH of 5-7. Viscosity enhancers such as PVP, HES or CMC may be optionally added. Acceptable injectable preserving agents such as methyl-4-hydroxybenzoate or propyl-4-hydroxybenzoate can also be added. Such solutions might be also used to treat an implantable medical device just before use by dipping or washing or rinsing.

Depending upon the indication, dispersions of one or more compounds might be used. Heparin/Protamine particles could prepared according to Mori (2010) in the presence of taurolidine or by adding tauroldine in a separate step, Mori et al. (2010), Mori Y, Nakamura S, Kishimoto S, Kawakami M, Suzuki S, Matsui T, Ishihara M, *International Journal of Nanomedicine Vol* 5, 147-155 (2010).

For topical application, a certain amount of alcohol such as, for example ethanol or isopropanol, without inducing flocculation of the protamine may be added, preferably below 40% (v/v) of the alcohol component if a solution is needed. Otherwise water for injection, hydrochloric acid to adjust the pH, macrogol 4000 and NaCl are preferred. Additional ingredients optionally include (3-amidopropyl cocoate) dimethylammonium acetate, sodium D gluconate, glycerol 85%, sodium chloride, and purified water.

Protamine sulfate solution 1% is compatible in 1 to 9 to 1:1 ratios with Lavasept concentrate (20% Polyhexanid and 1% Macrogol 4000) or with Octenisept. Taurolidine can be dissolved in the mixture to give a final concentration of 2% taurolidine.

In order to coat an implantable medical device before packaging to provide a coated device of the present invention, several types of coating solutions may be utilized containing the antimicrobial compositions of the present invention depending upon the desired results, coating processes, application, etc. A coating composition without a binder or with a water soluble binder such as PVP, PEG, CMC, HES, Dextran, Pluronics, Chremophors can be utilized and made from a mixture of taurolidine/protamine in water. If a coating concentration greater than 2% wt. % taurolidine is required, taurolidine can be dissolved in acetone/water 90/10-70/30 for up to 4% wt. % and then the implant is initially coated with taurolidine. If a polymeric binder is desired or required such as PLA or PLGA, the polymer may be additionally dissolved in the acetone/water mixture. In a second step the protamine solution is coated basically from water. The coating steps might be switched and an interim drying step might be added. The amount of optional polymeric binder used in the coating compositions will be sufficient to provide effective release of the taurolidine and additionally ensure sufficient mechanical stability during handling.

Compounding of the antimicrobial compositions of the present invention with resins may be performed whereby the ratio of taurolidine to bulk polymer (e.g., polydioxanone) for a surgical mesh should be higher than 30% wt. % to 70% wt. %, preferably higher than 50 wt. % to 50 wt. % drug to polymer to ensure a sufficient high release rate. For bone implants, higher polymer ratios might be used to ensure a slower release and prolonged action. A mixture of taurolidine/protamine is preferably compounded with polydioxanone below 150° C. and preferably under a protective gas atmosphere such as nitrogen or argon. The compound can be transformed into different shapes, including medical devices, using conventional processes such as injection molding and extrusion, or applied to a medical device by conventional processes such as gluing, stitching, knitting, melting, etc. One preferred formulation technique is according to EP1251794, incorporated by reference, in Example 16, where small balls are introduced into an implantable cord. 1 mm to 3 mm balls can be prepared either by compounding, by tableting or incorporating into capsules. The implant is preferably absorbable and may be used, for example, as an alternate antibiotic-free form for the Septopal Chain™ system for osteomyelitis.

In another embodiment of the present invention, the antimicrobial compositions of the present invention are encapsulated between two films, which may have pores of appropriate sizes to contain the antimicrobial composition and ensure a sufficiently effective release. The antimicrobial compositions of the present invention may be contained in a fabric pouch made from absorbable polymers, preferred are woven or non woven materials having tiny pores to prevent powdering out of the containment.

For some indications it is beneficial to optionally use additional active agents in combination with the antimicrobial compositions of the present invention. Selection and utilization of an active agent in combination with the compositions of the present invention depends upon the desired benefit intended to be derived. For example, it may be advantageous to provide an implant (either coated or compounded) comprising an antimicrobial composition according to the invention that has at least one additional biologically active ingredient or agent, which can optionally be released locally after the implantation. Substances which are suitable as active agents may be naturally occurring or synthetic and include and are not limited to, for example, antibiotics, antimicrobials, antibacterials, antiseptics, chemotherapeutics, cytostatics, metastasis inhibitors, antidiabetics, antimycotics, gynaecological agents, urological agents, antiallergic agents, sexual hormones, sexual hormone inhibitors, haemostyptics, hormones, peptide-hormones, antidepressants, vitamins such as Vitamin C, antihistamines, naked DNA, plasmid DNA, cationic DNA complexes, RNA, cell constituents, vaccines, cells occurring naturally in the body or genetically modified cells. The active agent may be present in an encapsulated form or in an adsorbed form. With such active agents, the patient prognosis can be improved according to the application or a therapeutic effect can be achieved (e.g., better wound healing, or inflammation inhibition or reduction).

Preferred as active agents are conventional antibiotics that include such agents as gentamicin or ZEVTERA™ (ceftobiprole medocaril) brand antibiotic (available from Basilea Pharmaceutica Ltd., Basel Switzerland). Most preferred is the use of highly effective, broad band antimicrobials against different bacteria and yeast (even in the presence of bodily fluids) such as octenidine, octenidine dihydrochloride (available as active ingredient in Octenisept® disinfectant from Schulke & Mayr, Norderstedt, Germany as), polyhexametliylene biguanide (PHMB) (available as active ingredient in Lavasept® from Braun, Switzerland), triclosan, copper (Cu), silver (Ag), nanosilver, gold (Au), selenium (Se), gallium (Ga), N-chlorotaurine, alcohol based antiseptics such as Listerine® mouthwash, N alpha-lauryl-L-arginine ethyl ester, ethyl-N-alpha-lauroyl-L-arginate hydrochloride, (LAE), myristamidopropyl dimethylamine (MAPD, available as an active ingredient in SCHERCODINE™ M), oleamidopropyl dimethylamine (OAPD, available as an active ingredient in SCHERCODINE™ O), and stearamidopropyl dimethylamine (SAPD, available as an active ingredient in SCHERCODINE™ S), and most preferably octenidine dihydrochloride (hereinafter referred to as octenidine) and PHMB.

The amounts of the optional active agents that may be present in the antimicrobial compositions of the present invention will be sufficient to effectively provide additional inhibition of bacterial colonization, biofilm formation thus reduce the risk of infection.

Additionally, a conventional contrast agent may optionally be incorporated into the antimicrobial compositions or antimicrobial coatings of the present invention. Such a contrast agent may be a biocompatible dye to create a visual marker as described in the EP1392198B1 or an agent such as a gas or gas creating substance for ultrasound contrast or MRI contrast, such as metal complexes like GdDTPA or superparamagnetic nanoparticles (Resovist™ or Endorem™) as taught in the EP 1324783 B 1. X-Ray visible substances (radiopaque) may optionally be included as shown in the EP1251794B 1 including pure zirconium dioxide, stabilized zirconium dioxide, zirconium nitride, zirconium carbide, tantalum, tantalum pentoxide, barium sulphate, silver, silver iodide, gold, platinum, palladium, iridium, copper, ferric oxides, not very magnetic implant steels, non-magnetic implant steels, titanium, alkali iodides, iodated aromatics, iodated aliphatics, iodated oligomers, iodated polymers, alloys of substances thereof capable of being alloyed, and the like.

The following examples are illustrative of the principles and practice of the present invention, although not limited thereto.

Example 1

Synergistic Mixture of Taurolidine+Protamine Sulfate on a Poly-g-Caprone Film Containing Hernia Mesh A poly-g-caprone film laminate mesh comparable to Ethicon's PhysioMesh hernia mesh product (available from Ethicon, Inc, Somerville, N.J. USA) but without a marker was prepared and punched out into 1.5 cm disks.

Taurolidine was dissolved at 4% wt./vol. in a 70% acetone 30% water vol./vol. mixture. Protamine sulfate was dissolved at 10% wt./vol. in water under warming. 50 µl of the taurolidine (TU) solution and 20 µl of the protamine (PS) solution were applied to each mesh disk using a pipette and allowed to dry at 50° C. until the majority of the liquid was gone and then stored under vacuum. First the taurolidine solution was applied, and then immediately thereafter the protamine sulfate solution was applied. The in vitro bacteria attachment assay was developed for its utility of indicating biofilm prevention potential of prototype mesh. Since bacterial attachment to a surface is the first step of biofilm formation, a surface treatment that inhibits bacterial attachment would reduce the chance of subsequent biofilm formation. The assay was conducted in SST (Serum Saline TSB) medium to mimic in vivo and clinical conditions. The formulation of SST is Tryptic Soy Broth (TSB):serum:saline in the ratio of 1:2:7. Each test article was incubated in SST inoculated with *Staphylococcus aureus* ACTT 6538 or *Escherichia coli* ATCC 25922 at about 6 Log CFU/ml. After incubation with rotation of 60 rpm for 4 hours at 37° C., the mesh discs were washed in saline 3 times to remove unattached bacteria. Bacteria attached to the mesh were collected by sonication in saline with neutralizing agent. Viable bacteria populations were measured by plate count on TSA (Tryptic Soy agar) medium contain neutralizing agents. The use of neutralizing agents in bacteria suspension and plate count medium was to eliminate any carry over antimicrobial effect from the coating. The plates were incubated at 37° C. for 24 hours. The number of attached viable bacteria was reported as CFU/disc.

The data in Table 1 indicated that mesh surfaces treated with the combination of TU and PS completely inhibited the attachment by *S. aureus* and *E. coli* in a serum containing media, while mesh surfaces treated with TU alone at the same dosage showed less inhibition than the combination.

TABLE 1

Viable Bacteria Attached to a Surgical Mesh (Ethicon PhysioMesh ® available from Ethicon, Inc.) Disc d = 1.5 cm after Four Hour Incubation in Bacteria/Serum Broth (pH = 7.4).

| Sample | TU (mg/disc) | PS (mg/disc) | CFU/disc S. aureus | CFU/disc E. coli |
|---|---|---|---|---|
| AB596 | 2 | 0 | 100 | 500 |
| AB597 | 2 | 2 | 0 | 0 |
| AB585 (Control) | 0 | 0 | 100,000 | 1,000,000 |

CFU: Colony forming unit

Example 2

Synergistic Bactericidal Composition of Taurolidine with Protamine Sulfate in Serum-Containing Medium (SST)

Concentration gradients of TU and PS were diluted in an SST medium and made into a two-dimensional matrix. Bacteria of interest were inoculated to the matrix at about 10e6 CFU/ml. *S. aureus* ACTT 6538 or *E. coli* ATCC 25922 were used for this Example 2. After incubation at 37° C. for 24 hours, viable bacteria populations were measured by plate count. Log reduction (LR) was used as the end point for efficacy and was defined as: Log CFU/ml of untreated control–Log CFU/ml of treated. Synergistic index (SI) was defined as LR of a given combination–sum of LR of single component at the same concentration as in the combination. SI=0 indicated additive effect, SI=1, indicated 90% more bacterial cidality, SI=2 indicated 99% more bacterial cidality, SI=3, indicated 99.9% more bacterial cidality, etc., by combination than its stand alone compositions at the same usage, thus synergy.

Figure 1:
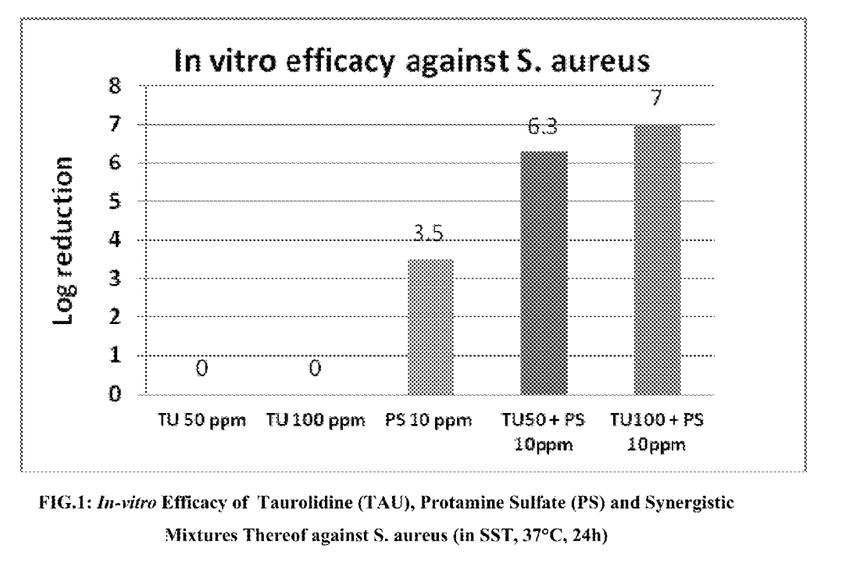
FIG. 1 is a graph showing the synergy of taurolidine and protamine sulfate by an in vitro efficacy assay against *S. aureus*.
Figure 2:
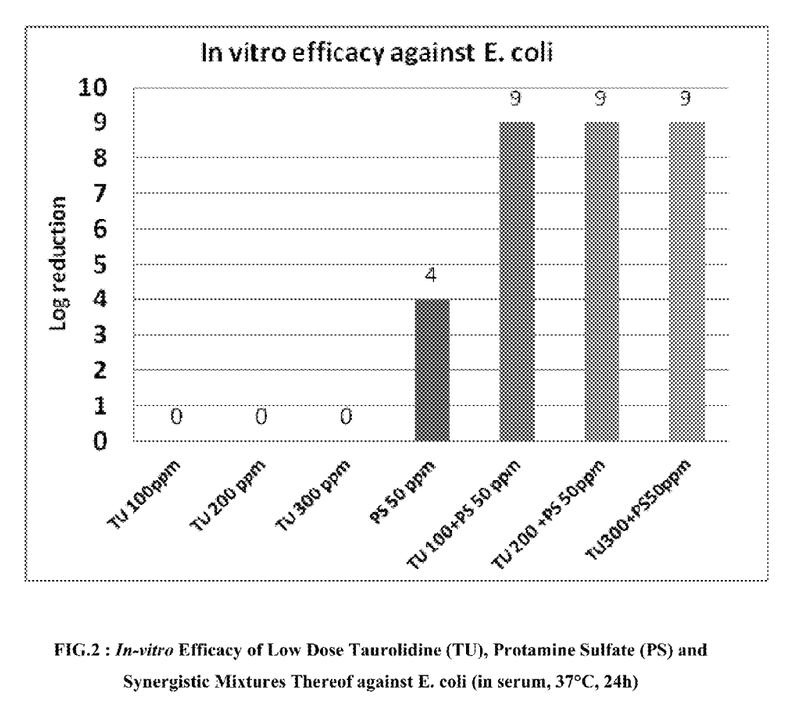
FIG. 2 is a graph showing the synergy of taurolidine and protamine sulfate by an in vitro efficacy assay against *E. coli*

A significant synergy was observed for the combination of protamine sulfate (PS) with taurolidine (TU) in serum-containing medium. When used alone, TU at 100 ppm showed no efficacy (LR=0) and PS at 10 ppm showed some efficacy (LR=3.5) against *S. aureus*. When combined 10 ppm PS with 50 ppm or 100 ppm TU, significant efficacy of 6 log reduction was achieved, as seen in the graph of FIG. 1. Also, a highly synergistic effect was shown for the mixture of TU+PS against *E. coli*, as seen in the graph of FIG. 2.

Example 3

In Vitro Efficacy of Surgical Implant Coated with Taurolidine+Protamine Sulfate

In accordance with Example 1, surgical mesh discs coated with different stand alone and combinations of taurolidine+protamine sulfate were prepared. Protocols of mesh coating and in vitro attachment assay as in Example 1 were used for this Example 3. The data is presented in Table 2.

TABLE 2

Bacterial Attachment (*S. aureus*) onto Composite Meshes Coated with Taurolidine or Mixtures of Taurolidine + Protamine Sulfate after 4 Hours in SST Medium at 37° C.

| TU/disc | PS/disc | Log reduction | Added log reduction* | Synergistic index (SI) |
|---|---|---|---|---|
| 500 µg | — | 1 | | |
| — | 50 µg | 0.4 | | |
| 500 µg | 50 µg | 1.5 | 1.4 | ~0.1 |
| 1000 µg | — | 0.8 | | |
| 1000 µg | 50 µg | >6 | 1.2 | >4.8 |
| 2000 µg | — | 2 | | |
| 2000 µg | 50 µg | >6 | 2.4 | >3.6 |

*The sum of log reduction of stand alone PS + log reduction of TU # Synergistic index (SI) was defined as LR of a given combination − sum of LR of single component at the same concentration as in the combination.
SI = 0 indicated additive effect, SI = 1, indicated 90% more bacterial cedality, SI = 2 indicated 99% more bacterial cedality, SI = 3, indicated 99.9% more bacterial cedality by combination than its stand alone composition at the same usage thus synergy.

The data in Table 2 showed a mild onset of a synergistic effect at a low TU dose of 0.5 mg/disc, the synergy is pronounced at higher loadings of 1.0 mg or 2 mg TU with 50 µg PS. An LR >6 and SI >3 at 1 mg and 2 mg TU plus 50 mg PS indicated that the combination completely inhibited *S. aureus* attached to the surface and the efficacy was shown to be >99.9% more than the sum of stand-alone efficacy.

Example 4

Synergistic Ratio of Protamine Sulfate (PS) and Taurolidine (TU)

The range of the ratios of the components of the synergistic antimicrobial compositions of the present invention was obtained by an in vitro MBC (minimum bactericidal concentration) study. The study was conducted in SST medium inoculated with about $10^6$ CFU/ml *Staphylococcus aureus* ACTT 6538. In vitro efficacy was evaluated for different ratios of PS and TU combinations along with the stand alone (i.e., individual) compositions at the same concentrations as in the combination composition. After incubation at 37° C. for 24 hours, viable bacteria populations were measured by plate count. Log reduction (LR) was used as the end point for efficacy and was defined as Log CFU/ml of untreated control−Log CFU/ml of treated. The synergistic index (SI) was defined as the LR of a given combination−sum of LR of single component at the same concentration as in the combination. An SI=0 indicated additive effect, SI=1, indicated 90% more bacterial cidality, SI=2 indicated 99% more bacterial cidality, SI=3, indicated 99.9% more bacterial cidality, etc., by a combination than its stand alone components at the same usage, thus synergy.

The data for this testing is presented in Table 3 and showed that synergistic combinations of PS and TU was in the range of 1:1 to 1:100. Ratios of TU and PS outside this range showed no synergy or less than its stand alone controls.

TABLE 3

In vitro Efficacy against *S. Aureus* by Log Reduction

| PS:TU (w/w) | LR-PS | LR-TU | LR-combination | Added efficacy | Synergy index |
|---|---|---|---|---|---|
| 50:1 | 3.1 | 0 | 2.9 | 3.1 | −0.2 |
| 10:1 | 3.1 | 0 | 2.7 | 3.1 | −0.4 |
| 1:1 | 3.1 | 0 | 4.5 | 3.1 | 1.4 |
| 1:10 | 0 | 0 | 6 | 0 | 6 |
| 1:50 | 0 | 0 | 4.7 | 0 | 4.7 |
| 1:100 | 0 | 0 | 1.3 | 0 | 1.3 |
| 1:200 | 0 | 0 | 0 | 0 | 0 |

A biofilm is an accumulation of microorganisms embedded in a polysaccharide matrix and adherent to a solid surface. Biofilms are clinically important, accounting for about eighty percent of hospital acquired infections. Biofilms are known to be extremely resistant to both immunological and antibiotic therapy. Microbial biofilms develop when microorganisms irreversibly adhere to a surface and produce extracellular polymers that facilitate adhesion and provide a structural matrix. The matured matrix is highly functional to protect microorganisms from adverse conditions while continually dispersing free cells to spread and colonize new surfaces. Therefore, inhibiting adhesion of bacteria to surfaces is important.

A medical device such as a mesh having an effective antimicrobial coating would effectively inhibit bacterial attachment to the surfaces of the devices, thus preventing or substantially inhibiting biofilm formation. The data in Examples 1 and 3 demonstrated the effectiveness of a synergistic composition of the present invention against bacteria attachment to a mesh prototype in a serum-containing medium. The data suggests promising benefits of using the synergistic composition to protect a medical device against biofilm formation.

The antimicrobial compositions of the present invention and medical devices coated with or containing such compositions have many advantages. The advantages include providing a synergistic antimicrobial composition with improved efficacy along with reduced usage. The reduced usage increases the safety margin, improves biocompatibility, improves physical device characteristics, and reduces material costs. A broader spectrum provided by the compositions of the present invention results in the compositions being an effective treatment against a wide range of microorganisms. The compositions of the present invention effectively inhibit bacteria attachment to surfaces of medical devices and help to prevent biofilm formation and related infections. There is no known bacterial resistance to taurolidine, and it is non-antibiotic. In addition, the compositions of the present invention are non-toxic, and approved for internal use.

Although this invention has been shown and described with respect to detailed embodiments thereof, it will be understood by those skilled in the art that various changes in form and detail thereof may be made without departing from the spirit and scope of the claimed invention.

We claim:

1. A coated medical device, comprising:
   a medical device having at least one surface; and,
   an antimicrobial coating on at least a part of said surface, wherein the coating comprises about 0.1 wt. % to about 10 wt. % of an antimicrobial composition, the composition comprising:
   about 50 wt. % to about 99 wt. % of taurolidine; and,
   about 1 wt. % to about 50 wt. % of protamine,
   wherein the antimicrobial composition has a synergistic index (SI) of greater than 1.

2. The coated medical device of claim 1, wherein the device comprises a mesh.

3. The medical device of claim 1, wherein the device comprises a polymer.

4. The medical device of claim 1, wherein the protamine comprises a protamine salt.

5. The medical device of claim 4, wherein the protamine salt comprises protamine sulfate.

6. The coated medical device of claim 1, wherein the antimicrobial composition comprises:
   about 70 wt. % to about 90 wt. % of taurolidine; and,
   about 10 wt. % to about 30 wt. % of protamine.

7. The medical device of claim 6, wherein the protamine comprises a protamine salt.

8. The medical device of claim 7, wherein the protamine salt comprises protamine sulfate.

9. The coated medical device of claim 1, wherein the antimicrobial coating additionally comprises an antibiotic.

10. The coated medical device of claim 9, wherein the antibiotic comprises gentamicin.

11. The coated medical device of claim 1, wherein the antimicrobial coating additionally comprises a polymeric binder.

12. The coated medical device of claim 11 wherein the polymeric binder is selected from the group consisting polylactides, polyglycolides, and copolymers thereof.

13. The medical device of claim 1, wherein the device is implantable.

* * * * *

SEQUENCE LISTING

<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Arg Arg Gly Gly Arg Arg Arg Arg
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Ser Arg Arg Arg Arg Arg Arg Gly Gly Arg Arg Arg Arg
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Arg Arg Arg Arg Arg
1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ser Arg Arg Arg Arg Arg Gly Gly Arg Arg Arg Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Arg Arg Arg Arg Ser Ser Pro Pro Arg
1               5                   10

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Arg Arg Arg Arg Arg His Ala Ser Thr Lys Leu Lys Arg Arg Arg
1               5                   10                  15

Arg Arg Arg His Gly Lys Lys Ser His Lys
            20                  25

<210> SEQ ID NO 7
<211> LENGTH: 30
<212> TYPE: PRT
<213> ORGANISM: Oncorhynchus mykiss

<400> SEQUENCE: 7

Pro Arg Arg Arg Arg Ala Ser Arg Arg Val Arg Arg Arg Arg Pro
1               5                   10                  15

Arg Val Ser Arg Arg Arg Arg Gly Gly Arg Arg Arg Arg Arg
            20                  25                  30

<210> SEQ ID NO 8
<211> LENGTH: 50
<212> TYPE: PRT
<213> ORGANISM: Rattus norvegicus

<400> SEQUENCE: 8

Ala Arg Tyr Arg Cys Cys Arg Ser Lys Ser Arg Ser Arg Cys Arg
1               5                   10                  15

Arg Arg Arg Arg Cys Arg Arg Arg Arg Arg Cys Cys Arg Arg Arg
                20                  25                  30

Arg Arg Arg Cys Cys Arg Arg Arg Ser Tyr Thr Phe Arg Cys Lys
            35                  40                  45

Arg Tyr
    50

<210> SEQ ID NO 9
<211> LENGTH: 48
<212> TYPE: PRT
<213> ORGANISM: Equus caballus

<400> SEQUENCE: 9

Ala Arg Tyr Arg Cys Cys Arg Ser Gln Ser Gln Ser Arg Cys Arg
1               5                   10                  15

Arg Arg Arg Arg Cys Arg Arg Arg Arg Arg Ser Val Arg Gln
                20                  25                  30

Arg Arg Val Cys Cys Arg Arg Tyr Thr Val Leu Arg Cys Arg Arg
            35                  40                  45

<210> SEQ ID NO 10
<211> LENGTH: 34
<212> TYPE: PRT
<213> ORGANISM: Dicentrarchus labrax

<400> SEQUENCE: 10

Pro Arg Arg Arg Arg Gln Ala Ser Arg Pro Val Arg Arg Arg Arg
1               5                   10                  15

Thr Arg Arg Ser Thr Ala Glu Arg Arg Arg Arg Val Val Arg Arg
            20                  25                  30

Arg Arg